United States Patent [19]

Bok et al.

[11] Patent Number: 4,459,354

[45] Date of Patent: Jul. 10, 1984

[54] CARBOHYDRASES FROM ACIDOPHILIC STREPTOMYCES

[75] Inventors: Song H. Bok, Decatur, Ill.; LeRoy E. Jackson, Ogden, Utah; Cynthia J. Schroedel, Brookfield; Martin Seidman, Decatur, both of Ill.

[73] Assignee: A. E. Staley Manufacturing Company, Decatur, Ill.

[21] Appl. No.: 432,173

[22] Filed: Oct. 1, 1982

Related U.S. Application Data

[62] Division of Ser. No. 64,321, Aug. 6, 1979, Pat. No. 4,399,222.

[51] Int. Cl.³ .................... C12P 19/24; C12N 9/92
[52] U.S. Cl. ........................................ 435/94; 435/234
[58] Field of Search ............... 435/94, 234, 99, 202, 435/886

[56] References Cited

U.S. PATENT DOCUMENTS 3,826,714 7/1974 Suekane ..................... 435/234 X 4,061,539 12/1977 Lee ................................ 435/850 X Primary Examiner—Lionel M. Shapiro
Attorney, Agent, or Firm—M. Paul Hendrickson; Philip L. Bateman; Forrest L. Collins

[57] ABSTRACT

Acidophilic and acidoduric streptomycetes strains have been found to produce carbohydrases. These *Streptomyces* effectively elaborate glucose isomerase under acid conditions typically unfavorable for growth of conventional glucose isomerase producing *Streptomyces*. Sterilization of the culture and production media may be avoided by selectively propagating newly discovered *Streptomyces acidodurans* under acidic conditions which will effectively eliminate contaminating micro-organisms. The *Streptomyces acidodurans* herein also have the ability to undergo cultivation and elaborate glucose isomerase over a relatively broad pH range. Constitutive streptomycetes strains have also been isolated. Glucose isomerases derived from these *Streptomyces* strains are particularly effective for isomerizing glucose syrups to fructose-containing syrups.

10 Claims, No Drawings

CARBOHYDRASES FROM ACIDOPHILIC STREPTOMYCES

CROSS-REFERENCE TO RELATED APPLICATIONS

This application is a division of application Ser. No. 06/064,321 filed on Aug. 6, 1979, now U.S. Pat. No. 4,399,222.

BACKGROUND OF THE INVENTION

High fructose syrups are commercially manufactured by enzymatically isomerizing dextrose syrups to a fructose containing syrup with glucose isomerase. Illustrative strains which reportedly possess commercial potential include *Actinoplanes missouriensis*, Arthrobacter sp., *Bacillus coagulans*, *Streptomyces albus*, *S. phaeochromogenes*, *S. olivaceus*, *S. olivochromogenes*, and *S. wedmorensis*.

Streptomycetes typically require relatively neutral culture media pH (e.g., >pH 6.0) for growth and glucose isomerase production. The above Streptomyces species cannot effectively grow and produce glucose isomerase at a pH less than 5.5.

Streptomycetes capable of growing under acidic conditions have been sparsely reported. Currently, these atypical Streptomyces species are regarded as a laboratory curiosity. An early report on an *Actinomyces acidophilus* (subsequently designated as *Streptomyces acidophilus*), which could be cultivated under acidic conditions (e.g., pH 4.0), had been isolated from Danish soil by Jensen (see *Soil Sci.* 25: 225–234, 1930). This streptomyces has been lost (e.g., see *Bergey's Manual of Determinative Bacteriology*—8th Ed., R. E. Buchanan and N. E. Gibbons co-editors—"no reference strains known"). Alexander (*Introduction to Soil Microbiology*, John Wiley & Sons, Inc., 1967) reports streptomycetes in slightly acidic environments will comprise less than 1% of the total viable bacterial count and they are essentially extinct in soils having a pH 5.0 or less. Recently Hagedorn (*Appl. Environ. Microbiol.* 32: 368–375, 1976) reported the isolation of acidophilic, acidoduric, and neutrophilic streptomycetes strains from acidic forest soils. The art failed to recognize that this atypical class of microorganisms produced commercially valuable enzymes. The difficulty in isolating these acidic streptomycetes (e.g., rare occurrence; presence of other predominant microorganisms; pH of culture media, etc.) may partially explain this lack of scientific interest and appreciation.

The inventors wished to explore the feasibility of obtaining valuable enzymes from these atypical Streptomyces. The microorganisms were unobtainable from public culture collections and depositories. Accordingly, wild-type Streptomyces for study purposes had to be isolated from a suitable source. During the course of such experimentation, it was unexpectedly discovered that these acid-loving Streptomyces elaborated glucose isomerase. By selective mutation, Streptomyces strains possessing significantly improved growth and glucose isomerase elaboration characteristics were subsequently discovered.

DESCRIPTION OF THE INVENTION

According to the present invention there is provided a method for producing glucose isomerase which comprises: (a) inoculating a culture medium containing assimilable carbon and nitrogen sources with microorganisms of the genus Streptomyces which will, under cultivation, produce glucose isomerase at a pH less than 5.5; (b) cultivating in inoculated medium for a period of time and under conditions sufficient to permit the microorganisms to produce glucose isomerase; and (c) harvesting the glucose isomerase produced by said microorganisms from said culture medium.

The glucose isomerase-producing Streptomyces of this invention are distinguishable from the other known, glucose isomerase-producing Streptomyces by their ability to grow and elaborate glucose isomerase in nutritive culture media maintained at a pH of less than 5.5. In general, these Streptomyces will typically undergo cultivation and elaborate glucose isomerase over a much broader pH range (e.g., between pH about 5 to about 9) than the known glucose isomerase-producing Streptomyces. Certain strains may be cultivated and produce glucose isomerase at even a more acidic pH (e.g., pH 4.0 or less). They may be selectively isolated from other bacteria by cultivating soil inoculants under acidic pH conditions (e.g., pH 5.2). The glucose isomerase efficacy of such Streptomyces strains may be determined by conventional glucose isomerase assay tests.

Although any wild strain of Streptomyces which is capable of growth and producing an analytically detectable amount of glucose isomerase may be considered to be a potential microbial source for the glucose isomerase-producing organisms of this invention, those wild strains which yield at least one gram of biologically pure culture per liter of culture media and at least 10 glucose isomerase units (GIU) per gram of dry cell are considered to be a more suitable microbial source than those of a lesser growth and glucose isomerase productivity. For commercial purposes, wild strains characterized as yielding at least 50 GIU/gram of dry cell substance (preferably at least 150 GIU/gram) and at least 3 dry cellular grams per liter (preferably at least 5 grams/liter) are best adapted as a glucose isomerase source or as a parent strain for mutants.

The capacity of these Streptomyces to produce glucose isomerase will vary considerably between different strains. In general, the glucose isomerase productivity of most wild strains may be improved upon by mutation (chemical and/or irradiation) and selectively culturing the mutants under conditions conducive to the propagation of the more productive strains thereof. By this technique, mutant Streptomyces strains exhibiting a several fold increase in productivity (e.g., about 4x to 100x or more) over the parent strain may be obtained. Likewise, the nutritional or enzymatic induction requirements may be altered or modified by mutation. Wild and ancestral strains requiring xylose for glucose isomerase production may be mutated into true constitutive strains (i.e., strains capable of producing glucose isomerase without xylose or xylan induction). From practial experience it has been found that the mild mutagens (U.V. light) generally produce more viable and productive strains than those obtained by more powerful mutagens (N-methyl-N'-nitro-N-nitrosoguanidine, etc.).

The Streptomyces strains and mutants contemplated under this invention advantageously include those Streptomyces capable of propagating and elaborating glucose isomerase at a pH 5.2 or less. These Streptomyces, in addition to being culturable at acidic pH's, generally have a broader growth and glucose isomerase elaboration pH range than the heretofore known glucose isomerase-producing Streptomyces strains. Potential microbial sources therefore include the glucose isomerase-producing streptomycetes such as isolated and reported by Jensen, Hagedorn, etc., as well as the newly discovered *Streptomyces acidodurans* reported herein, etc. Because these newly discovered biologically pure species are durable and culturable under very acidic pH's, it is deemed appropriate to name this new species as *S. acidodurans*. This new species characteristically grow and produce glucose isomerase at pH 5.0. However, the optimum pH for growth and glucose isomerase production typically ranges between about pH 6.0 to about 7.0 with an optimum pH 6.5±0.3 being most typical.

Illustrative *Streptomyces acidodurans* (wild species prefaced by *) and *Streptomyces acidodurans* mutants include *S. acidodurans NRRL 11489, *S. acidodurans NRRL 11496, S. acidodurans NRRL 11490, S. acidodurans NRRL 11491, S. acidodurans NRRL 11492, S. acidodurans NRRL 11493, S. acidodurans NRRL 11494, S. acidodurans NRRL 11495, S. acidodurans NRRL 11497 and S. acidodurans NRRL 11498.

The taxonomic characteristics of the organisms were determined according to the methods recommended by the International Streptomyces Projects ("Methods for Characterization of Streptomyces Species", E. B. Shirling and D. Gottlieb, *Intern. J. Syst. Bacteriol.* 16: 313-340, 1966), hereinafter referred to as IJSB.

I. Spores not borne on verticillate sporphores
   Medium (BYE) containing (gms./l): yeast extract—1.0; beef extract—1.0; tryptone—2.0; glucose—10; agar—15.
II. Melanoid pigments not produced (Pg. 334-IJSB)
    Peptone/yeast extract/iron/agar or tryosine agar. Pigments also absent in tryptone yeast agar and broth. Diffusible soluble pigments are not produced.
III. Smooth spore surface (pg. 329-IJSB)
     Henrici slide cultures were prepared with BYE and a casein/starch/agar ("Selection of Media for the Isolation of Streptomycetes", E. Küsner and S. T. Williams, NATURE 202: 928-929, 1964). After seven days (28° C.) smooth spore surfaces (1,000 x magnification) were observed.
     More luxuriant spore formation occurred with BYE and casein/starch/agar.
     Transmission electron microscopy reveals a smooth spore surface.
IV. Color of mature sporulated aerial mycelium is gray
    Seven days incubation at 28° C. on yeast extract/malt extract/agar (see pgs. 329-331, IJSB); tryosine agar; BYE, and casein starch agar.
V. Spore chain arrangement in spira
   Spores (Henrici slide) are simple spirals in chains of more than 10 (see pg. 328, IJSB).
VI. Utilization of carbon compounds
    All cultures were found to readily utilize the following sugars as a sole carbon and energy source in minimal salts media (see pg. 335, IJSB): glucose, xylose, arabinose, fructose, galactose and mannitol. Generally sucrose, raffinose, inositol, and salicin were degraded more slowly.

None of the *S. acidodurans* were able to utilize rhamnose, as a carbohydrate source. In addition, *S. acidodurans* NRRL 11492 utilize salicin, Wild *S. acidodurans* NRRL 11496 could not utilize inositol.

The aforementioned *Streptomyces acidodurans* species are merely representative of a much broader class of Streptomyces capable of producing glucose isomerase under acidic conditions. Numerous other glucose isomerase-producing wild strains and mutants have been discovered to exist. Streptomyces *NRRL 11489 and *NRRL 11496 were respectively capable of producing at least 80 GIU/gram and at least 500 GIU/gram. *S. acidodurans* NRRL 11489 (a wild strain isolated at a pH 3.5) will grow and elaborate glucose isomerase throughout the pH 5.0-9.0 range. The other wild strain (NRRL 11496) was isolated from a soil inoculant cultivated at pH 4.0. This highly acid resistant strain may be cultivated and will produce glucose isomerase throughout the pH 4.0-9.0 range. The mutant species of NRRL 11489 identified as NRRL 11490, NRRL 11491, NRRL 11492 and NRRL 11493 respectively producing about 150-200 GIU, about 150-200 GIU, at least 500 GIU and at least 690 GIU/gram and require xylose for glucose isomerase elaboration throughout the pH 5.0-10 range.

The species respectively identified by NRRL numbers 11494, 11495, 11497 and 11498 are capable of growth and elaborating glucose isomerase when corn steep liquor is utilized as the sole carbohydrate and nitrogen source. The NRRL 11494 (50 GIU/gram), NRRL 11497 (500-700 GIU/gram) and NRRL 11498 (500-700 GIU/gram) species are constitutive strains.

The *S. acidodurans* may be cultivated in a wide variety of culture media (solid or liquid) containing inorganic and/or organic assimilable nitrogen source materials and assimilable carbon source materials under aerobic conditions. Illustrative organic nitrogen sources of a water-soluble type include urea, peptone, meat extract, yeast extract, malt extract, corn steep liquor, casein hydrolyzates, fish meal, vegetable hydrolyzates (e.g., soybeans, cotton seeds, peanuts), cereal proteinaceous materials (e.g., wheat, bran, rice, corn protein, etc.), amino acids (e.g., glycine, glutamic acid, aspartic acid, alanine, etc.), mixtures thereof and the like. Illustrative inorganic assimilable nitrogen materials include ammonia, ammonium salts (e.g., ammonium chloride, ammonium nitrate, ammonium carbonate, ammonium acetate, ammonium sulfates), ammonium phosphate, the alkali nitrates (e.g., sodium nitrate), mixtures thereof and other similar water-soluble nitrogen containing salts. Illustrative sources of an assimilable carbon include fermentable sugars (e.g., glucose, xylose, arabinose, fructose, galactose, mannitol, lactose, sucrose, raffinose, salicin, inositol, maltose, ribose, etc.), glycerol, sorbitol and polysaccharides such as starch and starch hydrolyzates, mixtures thereof and the like.

The fermentation pH is appropriately adjusted to optimize the glucose isomerase yield for each strain. For some strains, a slightly alkaline pH will optimize glucose isomerase yields while other strains are more productive at acidic pH. Other strains are less pH sensitive and will effectively produce glucose isomerase at both acidic and alkaline pH. Certain other *S. acidodurans* strains (e.g., 11489 and 11496) are capable of producing high or optimum glucose isomerase yields under low acidic pHs (e.g., 4.0 to 5.5).

As commonly understood by the art, conventional acids (e.g., hydrochloric, phosphoric, sulfuric, citric, lactic, etc.) and bases (e.g., the alkali and alkaline earth metal hydroxides, certain amines, ammonia, etc.) and may be utilized to adjust the fermentation medium to its optimum. Conventional buffers (e.g., phosphate, acetate, etc.) may be used to maintain the fermentation medium at its optimum pH. Similarly, the pH may be controlled during the fermentation by periodic addition of an appropriate neutralizing agent.

As a general rule, most bacteria do not grow well at pH 5 or less. Bacteria which are capable of undergoing cultivation at pH 5 or less are the exception. The capacity of certain *S. acidodurans* strains herein to effectively grow and produce glucose isomerase at an acidic pH generally unfavorable to microbial growth affords definitive fermentation advantages. Contamination of the fermentation medium with interfering and undesirable microbes can be effectively avoided. Costly sterilization of the ferment broth and fermentor as well as the sterile precautions typically required to prevent microbial contamination (e.g., sterile aeration, etc.) are unnecessary. These *S. acidodurans* will effectively retain a true culture throughout the entire fermentation cycle. Sterility of the fermentation broth against undesirable microbial contamination is accomplished by the highly acidic fermentation pH. For other *S. acidodurans* strains requiring a more neutral or alkaline optimum pH, conventional techniques for providing and maintaining a sterile fermentation are employed.

The fermentation temperature is appropriately maintained to permit growth and glucose isomerase production (e.g., 20°–40° C.). Temperatures of about 25° C. to about 35° C., and preferably from about 30° C.±2° C., are particularly effective for this purpose.

A maximal glucose isomerase yield is generally achieved within a prescribed fermentation time for each strain and media. Although the fermentation time may vary considerably (e.g., about 10 to about 100 hours, depending upon strain type and the culture media), most Streptomyces strains herein achieve a maximal glucose isomerase yield within a very short time. Deviation from the maximal time (e.g., prolonged or insufficient fermentation) typically results in a decreased glucose isomerase yield. For most Streptomyces strains herein, maximum glucose isomerase yields will occur within 15 to 30 hours, with a fermentation time of about 20 to 25 hours being most typical.

Similar to all microorganisms, certain trace elements are needed for effective growth and propagation of the microorganisms of this invention. Illustrative trace elements found to be effective in propagating microbial growth include magnesium, iron, sulfur, phosphorous, potassium, sodium, mixtures thereof and the like. Corn steep liquor is particularly effective for microbial growth and enhancing glucose isomerase yields. Crude corn steep liquor treated to remove the acid-soluble and base-insoluble constituents therefrom typically provides a several-fold increase in glucose isomerase yields. Such base-insoluble constituents may be precipitated from the corn steep liquor by adjusting it to a neutral or basic pH (e.g., pH 6 to 8) with conventional bases (e.g., alkali, alkaline hydroxides, amines, ammonia, etc.). These precipitated constituents are separated from the corn steep liquor which makes it substantially free from such base-insoluble contaminants. The amount of corn steep liquor should be sufficient to enhance the glucose isomerase yield. Illustrative amounts therefore range from about 3 to about 40 gms/liter with about 10 to about 20 gms/liter being particularly effective for optimizing glucose isomerase yields.

The presence of a small amount of xylose or a xylose source material (e.g., hydrolyzed xylose or cellulosic substances such as straw, corn bran, sawdust, cereal and leguminous hulls, etc.) will also generally increase the glucose isomerase yield. This enhanced glucose isomerase productivity in the presence of xylose, generally applies also to some of the constitutive strains thereof. In general, he level of xylose in the fermentation will range from about 0 to about 30 gms/l and preferably from about 5 to about 10 gms/l.

The glucose isomerase may be directly recovered from the fermentor and, if desired, modified into a form most appropriate for its use in the isomerization of dextrose to fructose. Essentially all of the glucose isomerase is tightly affixed or superficially bound to the Streptomyces cells. Because the fermentation liquor is typically substantially free from water-soluble glucose isomerase, separation and recovery of glucose isomerase is relatively easy. The cell-bound glucose isomerase may be directly recovered and used to isomerize dextrose to fructose. When exposed to conditions conductive to enzymatic activity, viable or unmodified Streptomyces cells are prone to autolysis which will cause the glucose isomerase to convert to a water-soluble form.

For most commercial applications, it is advantageous to stabilize the glucose isomerase. This may be effectively accomplished by immobilizing the enzyme. The glucose isomerase may be immobilized by a wide variety of conventional immobilizing techniques. During its immobilization, processing conditions which tend to degrade or inactivate should be avoided.

The glucose isomerase may be immobilized in situ along with Streptomyces, or the cellular debris, or upon any other suitable immobilizing carrier. Illustrative means for immobilizing the glucose isomerase in situ to the Streptomyces cells include U.S. Pat. Nos. 3,654,080—Bengtson et al.; U.S. Pat. No. 3,753,858—Takasaki et al.; U.S. Pat. No. 3,779,869—M. F. Zienty; U.S. Pat. No. 3,821,082—Lamm et al.; U.S. Pat. No. 3,821,086—Lee et al.; U.S. Pat. No. 3,843,442—G. J. Moskowitz; and 3,909,355—Littlejohn et al.

Recovery of the optimum glucose isomerase activity from the fermentation broth, however, is best achieved by initially separating the glucose isomerase-rich, cellular material therefrom (e.g., filtration, decantation, centrifugation, washing, etc.), extracting or releasing the superficially-bound glucose isomerase from the cellular material and then immobilizing the glucose isomerase upon a suitable carrier therefor. The cell-bound enzyme may be extracted or released from the Streptomyces cells by conventional means such as autolysis, chemical or enzymatic lysis, treating of the cellular material with concentrated aqueous surface active agent solutions, homogenization, sonication, combinations thereof and the like.

The released or extracted glucose isomerase may then be immobilized to a suitable inert carrier by a wide variety of conventional immobilizing techniques (e.g., see U.S. Patent Office Class 195, subclasses 63–68 patents). Illustrative techniques for immobilizing glucose isomerase reported by the literature include: U.S. Pat. Nos. 3,708,397—T. Sipos; U.S. Pat. No. 3,767,531—Olson et al.; U.S. Pat. No. 3,783,101—Tomb et al.; U.S. Pat. No. 3,788,945—Thompson et al.; U.S. Pat. No. 3,838,007—A. G. van Belzen; U.S. Pat. No. 3,841,969—Emery et al.; U.S. Pat. No. 3,843,446—Vieth et al.; U.S. Pat. No. 3,860,486—Keys et al.; U.S. Pat. No. 3,868,304—R. A. Messing; U.S. Pat. No. 3,960,663—Tamura et al.; U.S. Pat. No. 3,965,035—Bialousz et al.; U.S. Pat. No. 4,025,667—Tomb et al.; German DT No. 2,303,872—assigned to Snamprogetti; German OLS No. 2,317,680—assigned to Novo Terapeutisk Laboratorium A/S; German Pat. No. 2,345,185—assigned to Novo Terapeutisk Laboratorium A/S; German DS No. 2,420,102—assigned to Tanebe Pharmaceutical KK; Netherlands Pat. No. 7,412,170—assigned to CPC International Inc., "Immobilized Enzymes Produce High Fructose Corn Syrup" N. H. Mermelstein, *Food Technology*, 29, 20, (1975), etc.

The glucose isomerases are useful for converting dextrose to fructose in conventional batch or continuous processes. Conventional metal ion activators (e.g., such as those having an atomic number of less than 28) may be incorporated into the dextrose feed syrup or isomerization media to activate and stabilize it against deactivation. The period 11a metal ions (e.g., magnesium) as well as metal ions of an atomic number 22–27 inclusive (particularly manganese, iron and cobalt) may be used for this purpose. As disclosed in U.S. Pat. No. 4,026,764 by Hurst, dry isomerase preparations may also be pretreated to enhance the glucose isomerase effectiveness and productivity in a continuous isomerization process.

The pH of the isomerization media is relatively broad (e.g., about 5.5 to about 9.5) for both batch and continuous operations. The isomerase activity rate is somewhat impaired at a pH of less than 6.5 while the more alkaline pH (e.g., greater than pH 8.5) are susceptible to undesirable color development. Overall isomerized syrup quality and enhanced fructose productivity will typically be best achieved by maintaining the isomerization media pH between about 6.5 to about 8.0 with the optimum pH for a continuous operation ranging from a pH 7.0 to about pH 8.0. Conventional buffers and/or antioxidants and/or preservatives may also be included within the isomerization media.

The glucose isomerase of this invention have excellent resistance towards thermal deactivation, especially when compared to those presently being used in the commercial manufacture of high fructose corn syrup. Such commercial glucose isomerases are almost completely deactivated after one hour use in a buffered 2–3M dextrose solution at 95° C. In contrast thereto, the glucose isomerase provided herein will still retain a substantial portion of its isomerization activity when exposed to identical isomerization conditions. The optimum activity temperature for the present glucose isomerase is also higher than those presently used to commercially manufacture high fructose corn syrups. This enhanced thermal stability enables the high fructose syrup manufacturer to operate at a higher temperature and thereby increase isomerase activity without thermally deactivating the glucose isomerase. In a continuous operation, this enhances column capacity (e.g., increased flow rates), glucose isomerase half-life and fructose productivity. Enzyme longevity and productivity will be realized even though the glucose isomerase may be utilized at a temperature well below its optimum.

Pragmatically the glucose isomerase herein may be effectively used to isomerize glucose to fructose over a relatively broad range (e.g., about 45° C. to about 85° C.). For most operations, the overall effectiveness of the enzyme (especially in continuous operations) is most suitably achieved by an operational temperature ranging from about 55° C. to about 75° C. and preferably at a temperature ranging from about 60° C. to about 70° C.

The *Streptomyces acidodurans* have also been found to produce enzymes other than glucose isomerase. The initial wild strains were discovered to possess amylase activity. Such amylases are capable of liquefying starches into starch hydrolyzates. Amylases derived from this new microbial source have a high starch liquefaction rate at an acidic pH range (e.g., 4.0–4.5). In contrast, the starch liquefying enzymes (e.g., bacterial alpha-amylase) presently employed in starch hydrolyzate manufacture typically require a much higher pH (e.g., about 5.5 to about 7.5) for effective starch liquefaction. These conventional liquefying bacterial alpha-amylases have a very slow rate of hydrolysis at such an acidic pH. The ability to effectively utilize these new amylases at more acidic pH makes them particularly useful in inhibiting the formation of retrograded starch and permits their combination with other amylases that have an optimum rate of hydrolysis at a similar pH level (e.g., glucoamylase).

The following examples are merely illustrative of the invention.

EXAMPLE I

A newly discovered wild strain, *Streptomyces acidodurans* NRRL 11489, was isolated in a mineral salts medium consisting of: $MgSO_4.7H_2O$—0.5 g/l, $KH_2PO_4$—3 g/l, $CaCl_2.2H_2O$—0.25 g/l, 2 mg/ml. starch and 1 mg/ml. corn steep solids and adjusted to pH 3.5 with 10N $H_2SO_4$. A 500 ml. Erlenmeyer flask containing 100 ml. of the medium was inoculated with one gram of garden soil and then incubated at 35° C. for 48 hrs. with shaking (New Brunswick Scientific, Model G-24 at 400 rpm). The soil sample (procured at Decatur, Ill.) had a pH of 6.4.

Following incubation, the suspension was streaked onto an agar medium of the same nutritive composition and pH as defined immediately above. After 24 hrs. cultivation at 35° C., the culture was examined for amylase-elaborating colonies as evidenced by hydrolysis of the starch. Starch hydrolysis was determined by the absence of the conventional blue iodine color. The only colonies displaying amylolysis were avidly adhering to the surface and powdery in nature. Representative amylase-elaborating colonies were isolated and preserved by lyophilization for further study.

One liter of the above mineral salts medium was then inoculated with the *S. acidodurans* NRRL 11489 and incubated with shaking for 18 hours at 35° C. Separately, ten liters of a fermentation medium having the same composition of the above mineral salts medium were prepared except the amount of starch was increased to 10.0 mg/ml. and the corn steep solids was replaced with 5 mg/ml. trypticase. The inoculant and fermentation medium were aseptically combined and adjusted from a pH 5.7 to a pH 4.9 with B 36N sulfuric acid. The inoculated fermentation medium was then fermented for 22 hrs. at 35° C. with 5.5 l. air/min. and 10 ml. antifoam M-8 (Hodag Chemical Corporation) to control foaming. The resultant cell mass was then removed from the fermentation broth by continuous centrifugation. The extracellular amylase of the culture broth was readily precipitated by cold isopropyl alcohol in a proportion of 2:1 (isopropyl alcohol to culture broth).

The resultant isopropyl alcohol/amylase precipitate was then assayed for alpha-amylase liquefying activity according to the Nelson-Somoygi colorimetric method. The substrate consisted of 1% pasted starch (weight basis) in 0.05M citrate/phosphate buffer. The substrate was mixed (1:1 substrate to amylase sample) and incubated for 20 minutes at 55° C. The amylase assayed at 0.083 units/mg.

The *S. acidodurans* NRRL 11489 was used to produce glucose isomerase as well as a parent strain for glucose isomerase producing mutants as illustrated below.

EXAMPLE 2

Soil samples (taken from a garden plot at Decatur, Ill.) were diluted under sterile conditions in sterile distilled water and plated onto an isolation agar medium consisting of: 1% glycerol, 0.2% $K_2HPO_4$, 0.005% $MgSO_4.7H_2O$, 0.003% $CaCO_3$, 0.2% NaCl, 0.001% $FeSO_4.7H_2O$, 0.03% casein, 0.2% citric acid and 2% agar (weight basis) with the agar medium then being adjusted to a pH 4.0. After autoclaving, antifungal antibiotics (cycloheximide and nystatin at a final conc. of 50 µg/ml.) were then added to the agar medium. The agar plates were incubated at 30° C. for one week. Colonies showing concentric rings with a powdery and leathery appearance were selectively isolated as Streptomyces strains. One of the isolated colonies was identified as *Streptomyces acidodurans* NRRL 11496. This strain was used to produce glucose isomerase as illustrated in Example 3.

EXAMPLE 3

The *Streptomyces acidodurans* NRRL 11489 and *S. acidodurans* NRRL 11496 of Examples 1 and 2 were then utilized to produce glucose isomerase. Each of the *S. acidodurans* strains was grown on a sporulation medium until heavy sporulation occurred. The sporulation media (weight basis) consisted of: yeast extract—0.4%, malt extract—0.3%, NaCl—0.5%, $MgSO_4.7H_2O$—0.05%, and bacto-agar—1.50%; and adjusted to pH 5.0 with 4N HCl.

Spores from each strain were then transferred to 100 ml. of production media in 500 ml. baffle-bottom Erlenmeyer flasks. The production media (pH 5.0) on a weight basis consisted of corn steep liquor (dry solids)—1.5%, citric acid—0.2%, $K_2HPO_4$—0.5%, $(NH_4)_2SO_4$—0.5%, $MgSO_4.7H_2O$—0.05%, and D-xylose—1.0%. Flasks were shaken on a rotary shaker (New Brunswick Scientific, Model G-24) at 450 rpm, 30° C. for 24 hrs. Cells were harvested by centrifugation for 10 minutes at 16,000×g (Sorval RC5 centrifuge, DuPont Instruments). The cells were washed twice with distilled water and freeze-dried. The resultant freeze-dried cell cultures were used as a glucose isomerase source.

Glucose isomerase activity was assayed by incubating dry cells with 30% glucose solution for 1 hr. at 65° C. in 0.05M maleate buffer, pH 6.6, with 0.01M $MgSO_4.7H_2O$ and 0.001M $CoCl_2.6H_2O$. The amount of fructose produced by glucose isomerase reaction was determined by liquid chromatography. One unit of glucose isomerase activity was defined as the amount of enzyme which can produce 1 µM fructose/min. at 65° C. and pH 6.60.

The *S. acidodurans* NRRL 11489 produced 5.0 grams of dry cells per ferment liter and 80 units of glucose isomerase per gram of dry cells (freeze-dried). The dry cell yield (i.e., 5.6 g/l) for the *S. acidodurans* NRRL 11496 was somewhat higher, but its activity of 500 glucose isomerase units (G.I.U.)/g dry cell has significantly greater than the *S. acidodurans* NRRL 11489.

The corn steep liquors used herein and in the following examples were prepared by neutralizing regular corn steep liquors to pH 7.0 with 4N NaOH and removing the resultant precipitates therefrom by centrifugation for 10 minutes at 16,000×g.

EXAMPLE 4

This example illustrates how ultraviolet (U.V.) irradiation of spore suspensions of *S. acidodurans* strains may be effectively utilized to significantly improve upon the glucose isomerase productivity of low producing *S. acidodurans* strains. The parent strain utilized in this example was *S. acidodurans* NRRL 11489. The number of successive U.V. mutations to achieve the high producing strains of *S. acidodurans* are specifically identified below by the term "generation". For each mutation, the spores were collected from an agar plate and transferred into 10 ml. of sterile water in a sterile petri dish. Each U.V. irradiation was conducted for 5 minutes at 30 cm. distance (4-watt U.V. lamp, Ultra-Violet Products, Inc., San Gabriel, Calif.). At least 90% kill occurred after each U.V. mutation treatment. The surviving spores were grown and isolated on the sporulation agar media as defined in Example 3.

Spores of *S. acidodurans* NRRL 11492 (a fourth generation U.V. mutant strain) were inoculated into a 100 ml. medium containing 0.2% sodium citrate, 0.5% $K_2HPO_4$, 0.5% $(NH_4)_2SO_4$, 0.05% $MgSO_4.7H_2O$, 0.01% $CoCl_2.6H_2O$, 0.001% $FeSO_4.7H_2O$, 0.5% NaCl, 1.5% corn steep liquor (dry solids), and 1% D-xylose at pH 5.0. The flask was shaken for 24 hrs. at 30° C. on a rotary shaker at 450 rpm. Cells were collected and freeze-dried. The *S. acidodurans* NRRL 11492 produced 4.1 g dry cells/liter and assayed at 519 G.I.U./cell g dry substance basis (d.s.b.).

Spores of *Streptomyces acidodurans* NRRL 11493 (a seventh generation U.V. mutant strain) were grown for 24 hrs. at pH 5.0 in a medium containing 0.2% sodium citrate, 0.5% $(NH_4)_2SO_4$, 0.05% $K_2HPO_4$, 0.05% $MgSO_4.7H_2O$, and 1.5% corn steep liquor (dry solids). The *S. acidodurans* NRRL 11493 produced 4.2 g dry cells/liter and assayed at 694 G.I.U./cell g (d.s.b.).

EXAMPLE 5

In this example constitutive mutant strains were derived from the *S. acidodurans* NRRL 11493 by the U.V. mutation methodology of Example 4. As a result, *S. acidodurans* NRRL 11494 (an eighth generation U.V. mutant) and *S. acidodurans* NRRL 11495 (a ninth generation U.V. mutant) were obtained. The production medium was the same as Example 3 except for the complete replacement of carbohydrate with the carbon source of Table I. The fermentation was conducted for 24 hrs. at 30° C. on a rotary shaker at 450 rpm. The resultant cells were collected and freeze-dried for glucose isomerase assay. Table I reports the results of this study.

TABLE I

| S. acidodurans | Carbon Source in the medium | g dry cells liter | G.I.U./g dry cells |
|---|---|---|---|
| NRRL 11494 | 1% xylose | 2.0 | 200 |
| NRRL 11494 | 1% sucrose | 1.0 | 59 |
| NRRL 11495 | 1% glucose | 3.6 | 327 |

Two different tenth generation constitutive mutants of *S. acidodurans* NRRL 11497 and NRRL 11498 (direct descendants of *S. acidodurans* NRRL 11495) were also isolated. One of these mutant strains (*S. acidodurans* NRRL 11497), was cultured in a medium solely consisting of a 3% (dry solids) whole corn steep liquor at a pH 7.0 and 30° C. for 48 hrs. The cells were collected by centrifugation and freeze-dried. The *S. acidodurans* NRRL 11497 produced glucose isomerase in the corn steep liquor media, without requiring other carbon or carbohydrate or nitrogen nutritive additives. The *S. acidodurans* NRRL 11497 was 215 G.I.U./gram dry cell solids and produced 19 g dry cells per liter.

The other tenth generation mutant (*S. acidodurans* NRRL 11498) was cultivated in a corn steep liquor/whey media containing 1.5% corn steep liquor, 3.0% whey, 0.7% NaCl, 0.05% MgSO₄.7H₂O, 0.5% cotton seed flour, pH 6.50. After 24 hrs. growth at 30° C., it yielded 16 g dry cells/liter and 330 G.I.U./g dry cell solids.

As illustrated above, the *S. acidodurans* NRRL 11494, NRRL 11495, NRRL 11497 and NRRL 11498 strains do not require xylose as an inducer to produce glucose isomerase.

EXAMPLE 6

This example illustrates the ability of the *S. acidodurans* strains to produce glucose isomerase over a broad pH range. In addition, the heat stability of the glucose isomerase at various temperatures, per the assay medium and methodology of Example 3 is shown below.

In this study, the wild *S. acidodurans* NRRL 11489 was used. In the pH studies, the *S. acidodurans* NRRL 11489 was grown for 24 hrs. in the Example 3 production media at various pH's as designated in Table II. The cells were collected and freeze-dried. The results of this study are reported in Table II.

TABLE II

| pH of the Medium | Dry Cell Yield (g/l) | Relative Glucose Isomerase Yield (%) |
|---|---|---|
| 4 | 0.3 | 2 |
| 5 | 6.1 | 100 |
| 6 | 6.7 | 92 |
| 7 | 6.8 | 85 |
| 8 | 8.0 | 92 |

As illustrated by the above data, *S. acidodurans* NRRL 11489 is capable of growing and producing glucose isomerase over a broad pH range, including highly acidic conditions. Its growth and glucose isomerase elaborating characteristics at a pH 5 or less are atypical of conventional glucose isomerase producing organisms.

The thermostability study results are reported in Table III.

TABLE III

| ENZYME REACTION TEMPERATURE (1 hr.) | RELATIVE GLUCOSE ISOMERASE ACTIVITY (%) |
|---|---|
| 60° C. | 70 |
| 65° C. | 100 |
| 70° C. | 124 |
| 75° C. | 165 |
| 80° C. | 200 |
| 85° C. | 280 |
| 90° C. | 340 |
| 95° C. | 220 |

As illustrated by the Table III data, the glucose isomerase derived from the *S. acidodurans* NRRL 11492 have exceptional thermostability. Glucose isomerases are generally prone to thermal deactivation or denaturation when exposed to 85° C. or higher assay temperatures for a short period of time. The optimum glucose isomerase activity temperature under the aforementioned assay conditions is at about 90° C. In general, conventional Streptomyces strain exhibit a considerably lower degree of glucose isomerase activity when exposed to assay temperatures of 90° C. or higher for a period of 1 hour or more.

The term "carbohydrase" is used to refer to those enzymes which will enzymatically attack or act upon a carbohydrate to cause a compositional or structural change to a carbohydrate molecule. This term includes amylases which will hydrolyze saccharides, enzymes which will isomerize saccharides as well as other enzymes which effectuate a structural or compositional change to saccharides. In a more limited embodiment of the invention, the term includes the polysaccharide hydrolyzing carbohydrases (e.g. starch, dextrins, maltodextrins, etc.) and the saccharide isomerizing enzymes such as glucose isomerase.

What is claimed is:

1. A glucose isomerase composition derived from bacteria of the genus Streptomyces characterized as:
    (a) retaining a substantial portion of glucose isomerase activity at a pH less than 5.2;
    (b) isomerizing glucose to fructose throughout the pH range of 5.0 to 9.0; and
    (c) having a glucose isomerase activity at 90° C. at least 3.0 times greater than its activity at 60° C., when assayed for one hour at pH 6.6 with a glucose solution consisting of 30 weight percent glucose, water, 0.05M maleate buffer, 0.01M M$_g$SO₄.7H₂O, and 0.001M CoCl₂.6H₂O.

2. The glucose isomerase composition of claim 1 wherein the isomerase is derived from bacteria of the species *Streptomyces acidodurans*.

3. The glucose isomerase composition of claim 2 wherein the isomerase is derived from a strain of bacteria of the species *Streptomyces acidodurans* selected from the group consisting of NRRL 11489, NRRL 11490, NRRL 11491, NRRL 11492, NRRL 11493, NRRL 11494, NRRL 11495, NRRL 11496, NRRL 11497, NRRL 11498, and mutants thereof.

4. The glucose isomerase composition of claim 3 wherein the isomerase is derived from *Streptomyces acidodurans* NRRL 11492.

5. A process for preparing fructose from glucose which comprises:
    (a) contacting the glucose isomerase of claim 1 with a glucose stream at a temperature of about 45° to 85° C. and a pH of about 6.5 to 8.5; and
    (b) recovering the fructose produced thereby until the activity of the glucose isomerase declines to a set percentage of its initial activity.

6. The process of claim 1 wherein the glucose isomerase is derived from bacteria of the species *Streptomyces acidodurans*.

7. The process of claim 2 wherein the glucose is contacted with the glucose isomerase while passing through a fixed bed of immobilized glucose isomerase.

8. The process of claim 3 wherein the glucose isomerase is derived from a strain of bacteria of the species *Streptomyces acidodurans* selected from the group consisting of NRRL 11489, NRRL 11490, NRRL 11491, NRRL 11492, NRRL 11493, NRRL 11494, NRRL 11495, NRRL 11496, NRRL 11497, NRRL 11498, and mutants thereof.

9. The process of claim 4 wherein the glucose isomerase is derived from a strain of bacteria of the species *Streptomyces acidodurans* selected from the group consisting of NRRL 11494, NRRL 11497, and NRRL 11498.

10. The process of claim 4 wherein the glucose isomerase is derived from *Streptomyces acidodurans* NRRL 11492.

* * * * *